United States Patent
Bhagwat et al.

(10) Patent No.: US 6,875,793 B2
(45) Date of Patent: Apr. 5, 2005

(54) ONCE-A-DAY CONTROLLED RELEASE SULFONYLUREA FORMULATION

(75) Inventors: Dileep Bhagwat, Bronxville, NY (US); Donald Diehl, II, Stony Point, NY (US); Anand R. Baichwal, Wappinger Falls, NY (US)

(73) Assignee: Penwest Pharmaceuticals Co., Patterson, NY (US)

( * ) Notice: Subject to any disclaimer, the term of this patent is extended or adjusted under 35 U.S.C. 154(b) by 22 days.

(21) Appl. No.: 10/396,114

(22) Filed: Mar. 25, 2003

(65) Prior Publication Data

US 2003/0219481 A1 Nov. 27, 2003

Related U.S. Application Data

(63) Continuation of application No. 09/479,465, filed on Jan. 7, 2000, now Pat. No. 6,537,578, which is a continuation of application No. 08/950,732, filed on Oct. 15, 1997, now Pat. No. 6,056,977.

(51) Int. Cl.[7] .................... A61K 31/4965; A61K 31/64; A61P 5/30
(52) U.S. Cl. .................... 514/593; 514/255.06; 514/866
(58) Field of Search ................................ 424/488, 468, 424/499, 500, 485, 458; 514/255.06, 593, 866

(56) References Cited

U.S. PATENT DOCUMENTS

| | | | |
|---|---|---|---|
| 3,485,847 A | 12/1969 | Bossert et al. | 260/295.5 |
| 3,784,684 A | 1/1974 | Bossert et al. | 424/37 |
| 4,191,772 A | 3/1980 | Woog et al. | 424/273 R |
| 4,346,709 A | 8/1982 | Schmitt | 128/260 |
| 4,412,986 A | 11/1983 | Kawata et al. | 424/80 |
| 4,562,069 A | 12/1985 | Hegasy et al. | 424/80 |
| 4,665,081 A | 5/1987 | Doi et al. | 514/356 |
| 4,673,564 A | 6/1987 | Kawata et al. | 424/494 |
| 4,696,815 A | 9/1987 | Schepky et al. | 424/80 |
| 4,764,382 A | 8/1988 | Kydonieus et al. | 424/449 |
| 4,765,989 A | 8/1988 | Wong et al. | 424/473 |
| 4,765,990 A | 8/1988 | Sugimoto et al. | 424/494 |
| 4,792,448 A | 12/1988 | Ranade | 424/438 |
| 4,792,450 A | 12/1988 | Kydonieus et al. | 424/449 |
| 4,792,452 A | 12/1988 | Howard et al. | 424/475 |
| 4,803,076 A | 2/1989 | Ranade | 424/438 |
| 4,803,081 A | 2/1989 | Falk et al. | 424/488 |
| 4,808,413 A | 2/1989 | Joshi et al. | 424/458 |
| 4,851,229 A | 7/1989 | Magruder et al. | 424/457 |
| 4,867,985 A | 9/1989 | Heafield et al. | 424/461 |
| 4,880,623 A | 11/1989 | Piergiorgio et al. | 424/78 |
| 4,889,723 A | 12/1989 | Kim et al. | 424/450 |
| 4,892,741 A | 1/1990 | Ohm et al. | 424/479 |
| 4,894,235 A | 1/1990 | Kohne et al. | 424/452 |
| 4,904,699 A | 2/1990 | Bauer | 514/972 |
| 4,940,587 A | 7/1990 | Jenkins et al. | 424/480 |
| 4,942,040 A | 7/1990 | Ragnarsson et al. | 424/486 |
| 4,973,469 A | 11/1990 | Mulligan et al. | 424/461 |
| 4,983,593 A | 1/1991 | Miyajima et al. | 514/110 |
| 4,994,276 A | 2/1991 | Baichwal et al. | 424/440 |
| 5,007,790 A | 4/1991 | Shell | 424/451 |
| 5,015,479 A | 5/1991 | Mulligan et al. | 424/457 |
| 5,019,397 A | 5/1991 | Wong et al. | 424/473 |
| 5,024,843 A | 6/1991 | Kuczynski et al. | 424/499 |
| 5,051,263 A | 9/1991 | Barry et al. | 424/490 |
| 5,071,642 A | 12/1991 | Lahr et al. | 424/474 |
| 5,071,643 A | 12/1991 | Yu et al. | 514/570 |
| 5,091,190 A | 2/1992 | Kuczynski et al. | 424/473 |
| 5,093,198 A | 3/1992 | Speaker et al. | 428/402.21 |
| 5,096,714 A | 3/1992 | Kuhrts | 424/439 |
| 5,100,669 A | 3/1992 | Hyon et al. | 424/426 |
| 5,108,757 A | 4/1992 | Erdos et al. | 424/451 |
| 5,110,602 A | 5/1992 | Kim et al. | 424/451 |
| 5,128,142 A | 7/1992 | Mulligan et al. | 424/457 |
| 5,128,143 A | 7/1992 | Baichwal et al. | 424/464 |
| 5,132,116 A | 7/1992 | Sournac et al. | 424/469 |
| 5,133,974 A | 7/1992 | Paradissis et al. | 424/480 |
| 5,135,757 A | 8/1992 | Baichwal et al. | 424/465 |
| 5,145,683 A | 9/1992 | Rhodes | 424/451 |
| 5,160,734 A | 11/1992 | Ganesan et al. | 424/78.38 |
| 5,169,638 A | 12/1992 | Dennis et al. | 424/457 |
| 5,169,639 A | 12/1992 | Baichwal et al. | 424/468 |
| 5,211,957 A | 5/1993 | Hagemann et al. | 424/466 |
| 5,215,758 A | 6/1993 | Krishnamurthy | 424/488 |
| 5,258,185 A | 11/1993 | Bauer et al. | 424/484 |
| 5,264,446 A | 11/1993 | Hegasy et al. | 514/356 |
| 5,264,459 A | 11/1993 | Chelmicka-Schorr et al. | 514/646 |
| 5,273,760 A | 12/1993 | Oshlack et al. | 424/480 |
| 5,286,493 A | 2/1994 | Oshlack et al. | 424/468 |
| 5,288,500 A | 2/1994 | Ibsen | 424/489 |
| 5,292,534 A | 3/1994 | Valentine et al. | 424/451 |
| 5,356,467 A | 10/1994 | Oshlack et al. | 106/153 |
| 5,415,871 A | 5/1995 | Pankhania et al. | 424/468 |
| 5,439,687 A | 8/1995 | Compassi | 424/468 |

(Continued)

FOREIGN PATENT DOCUMENTS

| | | | |
|---|---|---|---|
| CA | 1288049 | 8/1991 | |
| CA | 2101680 A1 | 2/1994 | A61K/31/44 |
| DE | 2714065 A1 | 10/1978 | A61K/9/10 |

(Continued)

OTHER PUBLICATIONS

Chemical Abstracts, vol. 104 (1986) Abstract 174662y.
Chemical Abstracts, vol. 99 (1983) Abstract 128360d.

(Continued)

*Primary Examiner*—Edward J. Webman
(74) *Attorney, Agent, or Firm*—Davidson, Davidson & Kappel, LLC

(57) ABSTRACT

This invention is directed to a novel solid matrixed controlled release, oral dosage form where the dosage form contains a therapeutically effective amount of a sulfonylurea or a salt or derivative thereof in the matrix. Further, the use of an aqueous alkalizing medium affords substantially complete bioavailability of the drug from the matrix of the tablet. The core tablets may optionally be coated with a coating material in the range of 2% to 10% with an enteric material or with a water insoluble material like ethyl cellulose.

41 Claims, No Drawings

U.S. PATENT DOCUMENTS

| | | | |
|---|---|---|---|
| 5,455,046 A | 10/1995 | Baichwal | 424/457 |
| 5,472,711 A | 12/1995 | Baichwal | 424/468 |
| 5,476,654 A | 12/1995 | Conte et al. | 424/78.08 |
| 5,478,574 A | 12/1995 | Baichwal et al. | 424/485 |
| 5,512,297 A | 4/1996 | Baichwal | 424/451 |
| 5,518,730 A | 5/1996 | Fuisz | 424/426 |
| 5,543,099 A | 8/1996 | Zhang et al. | 264/115 |
| 5,554,387 A | 9/1996 | Baichwal | 424/488 |
| 5,629,003 A | 5/1997 | Horstmann et al. | 424/401 |
| 5,662,933 A | 9/1997 | Baichwal et al. | 424/457 |
| 5,667,801 A | 9/1997 | Baichwal | 424/457 |
| 5,670,168 A | 9/1997 | Baichwal et al. | 424/464 |
| 5,773,025 A | 6/1998 | Baichwal | 424/458 |
| 5,830,497 A | 11/1998 | Yamanaka et al. | 424/448 |
| 5,846,563 A | 12/1998 | Baichwal | 424/457 |
| 6,048,548 A | 4/2000 | Baichwal | 424/468 |
| 6,245,355 B1 | 6/2001 | Baichwal | 424/468 |

FOREIGN PATENT DOCUMENTS

| | | | | |
|---|---|---|---|---|
| DE | | 3400106 A1 | 7/1985 | A61K/9/00 |
| EP | | 0147171 A2 | 7/1985 | C07D/401/12 |
| EP | | 0234670 B1 | 2/1987 | |
| EP | | 0357793 A1 | 3/1990 | |
| EP | | 460588 A | 12/1991 | |
| EP | | 0047899 A1 | 2/1996 | A61K/9/14 |
| EP | | 0232155 A2 | 8/1997 | |
| GB | | 2160100 A | 12/1995 | A61K/9/22 |
| WO | | 8504100 A1 | 9/1985 | A61K/9/40 |
| WO | WO 8902738 | | 4/1989 | |
| WO | WO 9206680 | | 4/1992 | |
| WO | | 9313773 A1 | 7/1993 | A61K/31/44 |
| WO | | 9423700 A1 | 10/1994 | A61K/9/16 |
| WO | | 9534582 | 12/1995 | A61K/9/00 |

OTHER PUBLICATIONS

Chemical Abstracts, vol. 92 (1980) Abstract 135278s.

Chemical Abstracts, vol. 92 (1980) Abstract 82429h.

Chemical Abstracts, vol. 77 (1972) Abstract 39130g.

Chemical Abstracts, vol. 70 (1969) Abstract 17133p.

Chemical Abstracts, vol. 98 (1983) Abstract 221832y.

Alderman, D.A., "A review of cellulose ethers in hydrophilic matrices for oral controlled–release dosage forms", *Int. J. Pharm. Tech. & Prod. Mfg.*, vol. 5, pp. 1–9 (1984).

Haynes, R. Brian, M.D., et al., "Manipulation of the therapeutic regimen to improve compliance: Conceptions and misconceptions", *Clinical Pharmacology and Therapeutics*, vol. 22, No. 2, (Aug. 1977).

English translation of Japanese Patent Laid–Open–To–Public, publication No. 8/1986, publication date Jan. 6, 1986, Japanese Patent Application No. 118,789/1984; Japanese Patent Application date: Jun. 9, 1984.

*Techniques of Solubilization of Drugs*, edited by Samuel H. Yalkowsky, The Upjohn Company, pub. Marcel Dekker, Inc., New York and Basel, pp. 308–315 (1981).

"Crystalliztion and Granulation", Remington's Practice of Pharmacy, 9th Ed. Chapter XXVII, pp. 208–211, 1950.

Ritschel, Angewandte Biopharmazie, pp. 293–302 (1973).

Sugimoto, I., et al., "Dissolution and Absorption of Nifedipine From Nifedipine–Polyvinylpyrrolidone Coprecipitate", *Drug Development and Industrial Pharmacy*, vol. 6, No. 2, pp., 137–161 (1980).

Kleinblosem, M., et al., Nifedipine: Kinetics and dynamics in healthy subjects, *Chin. Pharmacol. Ther.*, Vo. 35, No. 6, pp. 742–749 (1984).

Ramasch, K., et al., "Pharmacokinetics and Metabolism of Nifediphine", *Hypertension Supplement II*, Vo. 5, No. 4, Jul.–Aug. 18–24 (1983).

McGinty, J.W., et al., "Dissolution and Uniformity Properties of Ordered Mixes of Micronized Griseofulvin and a Directly Compressible Excipient", *Drug Development and Industrial Pharmacy*, vol. 11, No. 4, pp. 891–900 (1985).

Helbig, J., et al., "Pharmaceutical oral dosage forms of an active agent capable of forming or releasing bicarbonate ions", *Pharmaceuticals*, (Abstract–98:221837d), vol. 98, p. 63 (1983).

*The Merck Index*, pp. 848–849, 9th Ed. (1976).

D.Q.M. Craig, "Polyethyelene Glycols and Drug Release", *Drug Development and Industrial Pharmacy*, 16(17), pp. 2501–2526 (1990).

English translation of Ritschel, Angewandte Blopharmazie, pp. 293–302 (1973).

Supplementary Partial European Search Report for European Application No. 98 95 3532.

ONCE-A-DAY CONTROLLED RELEASE SULFONYLUREA FORMULATION

This application is a continuation of U.S. application Ser. No. 09/479,465 filed Jan. 7, 2000, now issued U.S. Pat. No. 6,537,578 which is a continuation application of U.S. application Ser. No. 08/950,732, filed Oct. 15, 1997, now issued U.S. Pat. No. 6,056,977.

FIELD OF THE INVENTION

The invention is directed to controlled release pharmaceutical formulations, and more particularly to controlled release formulations incorporating sulfonylurea and derivative compounds which are suitable for 24 hour administration to a patient in need of treatment related thereto.

BACKGROUND OF THE INVENTION

The advantages of controlled release products are well known and documented in the pharmaceutical art. Advantages include the ability to maintain a desirable blood level of a medicament over an extended period, such as twenty four hours, by minimizing the peak to trough variations in plasma concentrations. Also, patient compliance is increased by reducing the number of administrations necessary to achieve a desired therapeutic effect. Oral controlled release delivery systems should ideally be adaptable so that release rates and profiles can be matched to physiological and chronotherapeutic requirements. While many controlled and sustained release formulations are already known, certain moderately to poorly soluble drugs present formulation difficulties which render them unsuitable for sustained release carriers which might be acceptable for other drugs, such as those that are relatively soluble. It is often impossible to predict whether a particular sustained release formulation will provide the desired release profile for a relatively insoluble drug, and it has generally been found that it is necessary to carry out considerable experimentation to obtain sustained release formulations having the desired bioavailability when ingested, particularly for drugs that are poorly soluble in water.

An example of relatively insoluble drugs which are difficult to formulate into controlled reelease formulations is the sulfonylurea class of antidiabetic drugs. Sulfonylureas are effective to control blood sugar levels in diabetics, in particular, type II diabetic patients who are unable to achieve control through dietary restriction alone. Sulfonylureas are believed to stimulate the release of insulin from the pancreatic islet cells via receptors that are reported to be ATP sensitive potassium channels.

In humans, acute stimulation of insulin secretion by sulfonylureas in response to a meal is believed to be of major importance, thus the sulfonylureas require endogenous insulin secretion in order to achieve beneficial results. Fasting insulin levels are not elevated even on long-term administration, but the postprandial insulin response continues to be enhanced after at least 6 months of treatment. The insulinotropic response to a meal occurs within 30 minutes after an oral dose of Glipizide (a sulfonylurea) in diabetic patients, but elevated insulin levels do not persist beyond the time of the meal challenge. It is also believed that extrapancreatic effects may play a part in the mechanism of action of oral sulfonylurea hypoglycemic drugs. For example, although the mechanism by which sulfonylureas lower blood glucose during long-term administration has not been clearly established, it has been reported that these drugs enhance the sensitivity of tissue insulin receptors after prolonged treatment. The subject is generally reviewed in Goodman and Gilman's, *The Pharmacological Basis of Therapeutics*, the disclosure of which is incorporated by reference herein in its entirety.

The sulfonylureas are considered to be subdivided into two subcategories: the first generation agents, e.g., tolbutamide, chlorpropamide, tolazamide, acetohexamide, and the second generation agents, e.g., glyburide (glibenclamide), glipizide and gliclazide.

Tolbutamide is practically insoluble in water but forms water-soluble salts with alkali. Tolbutamide is commercially available in 250 mg or 500 mg immediate release tablets. The immediate release formulation is typically administered twice to three times a day.

Tolazamide is also relatively insoluble in water. The solubility at pH 6.0 (mean urinary pH) is 27.8 mg per 100 ml. Tolazamide is commercially available in 100 and 250 mg immediate release tablets. The immediate release formulation is typically administered twice a day. Acetohexamide practically insoluble in water and ether, soluble in pyridine and dilute solutions of alkali hydroxides, and slightly soluble in alcohol and chloroform. Acetohexamide is commercially available in 250 and 500 mg, immediate release tablets. The immediate release formulation is typically administered twice a day.

Chlorpropamide is soluble in water at pH 6.0 (2.2 mg/ml) and practically non-soluble in water at pH 7.3.

Glyburide is sparingly soluble in water and soluble in organic solvents. Glyburide is available as tablets of 1.25 mg, 2.5 mg. and 5 mg strengths for oral administration and is typically administered twice a day.

Glipizide is insoluble in water and alcohol but soluble in alkali, e.g., 0.1N sodium hydroxide. The immediate release formulation is typically administered twice a day.

The first generation agents vary widely in their pharmacokinetics, with acetohexamide, tolbutamide and tolazamide having a half-life of about 4 to 7 hours, necessitating repeated doses throughout the day, whereas chlorpropamide has a half life of from 24 to 48 hours. The second generation agents are about a hundred times more potent, by weight, than are the first generation agents, but generally have a shorter half-life, ranging from about 1.5 to 5 hours.

Glipizide, is representative of the second generation sulfonylureas. Gastrointestinal absorption of glipizide is uniform, rapid and essentially complete, providing peak plasma levels concentrations about 1 to 3 hours after a single oral dose. Normal subjects demonstrate an elimination half-life ranging from about 2 to about 4 hours after both intravenous and oral administration. In addition, glipizide does not accumulate in the plasma following repeated oral dosing. Glipizide tablets are available, e.g., in 5 and 10 mg immediate release formulations (e.g., as Glucotrol®, marketed by Pratt Pharmaceuticals).

Immediate release tablets formulated with a sulfonylurea based on an acidified and/or alkalized excipient and an inert polar solvent, such as polyethylene glycol, are described by U.S. Pat. No. 4,696,815. These pH regulated, immediate release formulations are described as improving the dissolution of acidic, amphoteric or basic antidiabetic sulfonylurea compounds, respectively. For example, the alkalized excipient is said to promote improved dissolution of glipizide, which is an acid compound. An analogous immediate release formulation with an acidified and/or alkalized excipient, an inert polar solvent and polyvinylpyrrolidone is also described by U.S. Pat. No. 4,696,815.

Erodible poly(orthoester) or poly(orthocarbonate) devices for implantation or insertion into a patient are described by U.S. Pat. No. 4,346,709, for delivering a drug in a controlled manner, including oral hypoglycemic drugs such as the sulfonylurea hypoglycemics, acetohexamide, glypinamide, chlorpropamide, tolazamide, tolbutamide, phenformin.

A controlled release delivery system using melt spun biodegradable polymers as a carrier or host material for a bio-effecting agent such as a pharmaceutical active or a hormonal compound, including glipizide, for e.g., oral administration, is described by U.S. Pat. No. 5,518,730.

Controlled release microspheres for administration by, e.g, the oral route and comprising polylactic acid and a water soluble physiologically active substance and having a mean particle size of from about 0.01 mu m to 300 mu m are described by U.S. Pat. No. 5,100,669 as including active substances such as the antidiabetic agents glipizide, glymidine sodium, phenformin hydrochloride, methformin, buformin hydrochloride.

Uniformity and predictability of therapeutic levels of sulfonylureas and resulting blood sugar levels are considered to be desirable in the management of diabetes patents, and in particular, for the management of type II diabetic patients. For example, in tests with art-known extended release glipizide (formulations based on orally ingestible osmotic devices, as discussed hereinbelow) it has been shown that fasting plasma glucose levels were significantly lower in patients treated with controlled release glipizide than with immediate-release glipizide (Berelowitz et al., 1994, *Diabetes Care* 17(12):1460–4).

Extended release sulfonylurea formulations with improved dissolution properties, and particularly, extended release formulations of second generation sulfonylureas, are therefore a desirable addition to the medical treatment of diabetes, including type II diabetes. Of these second generation drugs, efforts to provide controlled release have focused on glipizide. Art-known extended release glipizide formulations are available as osmotic based dosage forms, such as, for example, Glucotrol XL Extended Release Tablets® (Pratt Pharmaceuticals; 5 to 60 mg unit doses). As with other art-known extended release glipizide, discussed hereinbelow, Glucotrol XL® is prepared as an osmotic pump formulation. Specifically, Glucotrol XL® is prepared as an osmotically active drug core surrounded by a semipermeable membrane. The core itself is divided into two layers: an "active" layer containing the drug, and a "push" layer containing pharmacologically inert (but osmotically active) components. The membrane surrounding the tablet is permeable to water but not to drug or osmotic excipients. As water from the gastrointestinal tract enters the osmotically active material, the tablet pressure increases in the osmotic layer and "pushes" against the drug layer, resulting in the release of drug through a small laser-drilled orifice in the membrane on the drug side of the tablet.

Other osmotic pump devices and formulations for administering glipizide are described in U.S. Pat. Nos. 5,091,190 and 5,024,843 (Kucrynski et. al.) and in U.S. Pat. No. 4,803,076 (Gautman). These patents describe the delivery of glipizide in a controlled manner by the use of an oral formulation based on another osmotic pump design. U.S. Pat. No. 4,792,448 (Gautman) has also described the zero order release of glipizide using a device described as a strip covered by an impermeable wall with uncovered areas. All of these formulations therefore are prepared from a plurality of osmotic pump devices that require complex manufacturing processes with attendant high costs.

Therefore, there has not previously been a fully satisfactory and economical formulation for providing a predictable and uniform treatment regimen, which avoids the need for the construction of complex devices for oral administration and that have the further advantage of simplifying treatment and improving patient compliance while both enhancing the bioavalability of the antidiabetic drug and prolonging the release of the drug.

A significant problem facing the pharmaceutical formulator attempting to prepare a bioavailable oral sustained release dosage form of a sulfonylurea relates to the ability of the dosage form to release the drug over the desired period of time to such an extent that the sulfonylurea content of the dosage form will be effectively bioavailable. One aspect of this problem is the fact that sulfonylureas are relatively insoluble and therefore inherently difficult to be solubilized from an oral dosage form in the gastrointestinal tract and then be absorbed through the walls of the gastrointestinal tract. This solubility and bioavailability problem has been overcome with respect to immediate release oral sulfonylurea dosage form by utilizing a solubilizing agent, as discussed above. However, such agents are expected to cause the fast, i.e., immediate, release of all of the sulfonylurea when orally administered. Therefore, the use of such solubilizing agents would not necessarily be considered desirable in sustained release oral dosage forms, where the goal is to slow the release of drug from the dosage form over an extended period of time.

Thus, there is a continuing need in the art for a relatively simple and economical controlled release sulfonylurea formulation for oral administration that is fully bioavailable and suitable for administration once every 24 hours.

SUMMARY OF THE INVENTION

The present invention is directed to a controlled release sulfonylurea antidiabetic formulation that is suitable for once-a-day or 24 hour administration and that is formulated into a solid sustained release matrix that includes an alkalizing or an acidifying medium affording substantially complete bioavailability from the sustained release matrix.

The present invention is also directed to an improved and more economical method for the stable and convenient treatment of diabetes of the type that is responsive to control by a sulfonylurea antidiabetic agent. Also the present invention is direcetd to a method for preparing a bioavailable controlled release 24 hour formulation for sulfonylurea drugs such as, e.g., glipizide.

Still yet further, the present invention is directed to a controlled release dosage form for oral administration comprising a therapeutically effective amount of Glipizide or a pharmaceutically acceptable salt thereof; and, a controlled release matrix comprising a gelling agent, an ionizable gel strength enhancing agent and an inert diluent; wherein the ratio of gelling agent to inert diluent is from about 1:8 to about 8:1; the gelling agent comprises xanthan gum and locust bean gum in a ratio of from about 3:1 to about 1:3; the ionizable gel strength enhancing agent increases the gel strength of the controlled release matrix; and, the Glipizide is suspended or dissolved in a pharmaceutically acceptable wetting agent prior to incorporation with the remaing ingredients of the controlled release matrix.

Also, the present invention is directed to a method of manufacturing a controlled release oral dosage form suitable for once a day administration of a Glipizide or a salt thereof comprising the steps of: a) granulating a controlled release matrix with an aqueous medium made alkaline by a pharmaceutically acceptable alkalizing agent present in an amount effective to provide a pH ranging from at least 7.0 to about 9.0 to produce a granulation; b) suspending, dissolving or admixing a sulfonylurea compound in a pharmaceutically acceptable wetting agent to form an active agent composition; c) mixing a suitable tableting lubricant, the active agent composition and said granulation to a lubricated granulation; and, d) compressing said lubricated granulation into a solid dosage form; wherein the sulfonylurea is selected from the group consisting of tolbutamide, chlorpropamide, tolazamide, acetohexamide, glyburide, glibornuride, glisoxepide, glipizide and gliclazide.

The present invention is also directed to a method of treating type II diabetes comprising administering an at least once a day a solid controlled release oral dosage form comprising: a) an effective amount of alkalized glipizide or a salt thereof, b) a controlled release matrix which has been granulated with an aqueous medium made alkaline by pharmaceutically acceptable alkalizing agent present in an amount effective to provide a pH ranging from at least 7.0 to about 9.0, wherein the controlled release oral dosage form provides a sustained release of glipizide over a period of 24 hours.

DETAILED DESCRIPTION OF THE INVENTION

The term "sustained release" as used herein, is meant release of active ingredient at such a rate that blood levels are maintained within the therapeutic range but below toxic levels over an extended period of time e.g., 12 to 24 hours or greater.

By "bioavailability" is meant the physiological availability of a given amount of a drug. For oral ingestion, this is based on the extent to which the active drug ingredient is released from the drug product and becomes available for absorption from the gastrointestinal tract. A formulation for oral ingestion that is substantially bioavailable allows for the release of substantially all of the incorporated drug in a form suitable for absorption by the gastrointestinal tract. The bioavalability can be measured, for example, by art known in vitro dissolution tests. As demonstrated by the examples below.

The term "insoluble" as used herein, unless otherwise stated, the term, "insoluble" encompasses drugs that are only soluble with more than 30 to 100 parts of solvent to one part of solute or drug.

An "acid agent" or excipient or "acidifying agent" or excipient is a pH modifying excipient that when added to the aqueous medium to be granulated with the polysaccharide release controlling material, will provide a pH of less than 7.0, ranging, for example, from about pH 5.0 or less to about pH 6.9 or from about pH 6.0 to about pH 6.9.

An "alkalizing agent" or excipient or "alkaline agent" or excipient as used herein is a pH modifying excipient that includes any pharmaceutically acceptable material that causes the pH of an aqueous medium, for use in granulating the release controlling polysaccharide, to rise above pH 7.0.

The present invention provides a controlled release oral dosage form that comprises a pharmaceutically effective amount of a sulfonylurea or a derivative or salt thereof, a controlled release matrix and optionally a coating.

The controlled release matrix is designed to provide continuous and prolonged release of glipizide over a period of from 12 to 24 hours. Most preferebly the dosage forms of the present invention will provide a release of about 15% after 2 hours, between 20% and 60% after 8 hours and greater than 65% after about 12 hours. Further, the active agent will preferably release 90% or more of the active agent after 20 hours.

Active agents for use in the present invention are sulfonyl urea compounds which may be first generation and second generation compounds including tolbutamide, chlorpropamide, tolazamide, acetohexamide, glyburide (glibenclamide), glipizide and gliclazide, their acids and salts, derivatives and combinations thereof. The preferred active ingredient is glipizide.

The amount of active ingredient to be included in the compositions of the present invention is effective to provide therapeutic, hyperglycemia controlled plasma levels in a patient in need thereof for at least 24 hours, or more. An effective dose will be readily determined by the artisan, based on the art known potency and properties of glipizide and fine-tuned by empirical titration of dose and clinical response. Factors which affect clinical response and may be used to estimate initial dosage levels include, e.g., patient mass, the degree of active agent based glycemic control that is required in a patient, the patient's responsiveness to active agent control, the patient's diet and exercise levels.

Typically the amount of active ingredient may vary from about 0.5 mg to about 40 mg. The preferred dosage of active ingredient according to the present invention is between 4 mg and 16 mg and most preferably between 5 mg and 10 mg.

Preferably, the active substance of the present invention, e.g., glipizide, is dispersed in an aqueous alkaline medium of at least pH 7.0, or more, to which is added a surfactant and/or a polar solvent such as a polyalkylene glycol, including a PEG, before incorporation into a controlled release matrix. In addition, a binding agent such as, for example, as polyvinylpyrrolidone ("PVP") may optionally be included in the aqueous medium.

The controlled release matrix is a solid formulation which allows for the prolonged or extended release of active agent at a rate sufficeient to maintain therapeutic blood levels of active agent. The controlled release matrix can makeup from about 40% to about 98% of the total weight of a unit dosage form, excluding coatings, according to the present invention. More preferably the controlled release matrix will make up from about 50% to about 95% of the total weight of the inventive compositions.

The controlled release matrix to active agent ratio can be from 5 to 1 to about 15 to 1, and compositions having integer ratios of all possible combinations between these ranges including 10 to 1 are considered embodiments of the present invention.

The controlled release matrix according to the present invention can include ingredients such as polysaccharides, cationic crosslinking agents, inert diluents, alkalizing agents, acidifying agents, surfactants, polar solvents and excipients.

The rate controlling matrix (also referred to as the "polysaccharide blend" or "polysaccharide mixture") can be any suitable material that forms a matrix which provides sustained release of an alkalized or acidified incorporated active agent, medicament or drug and the like. Pharmaceutically acceptable rate controlling materials which may be used in the present invention include both synthetic and naturally occurring gums and/or polymers and other art-known rate controlling substances. Examples include naturally occurring or modified naturally occurring or synthetic or semi-synthetic polymers or gums such as, e.g., alginates, carrageenan, pectin, xanthan gum, locust bean gum, guar gum, modified starch, alkylcellulose, hydroxypropylmethylcellulose, methylcellulose, and other cellulosic materials or polymers, such as sodium carboxymethylcellulose and hydroxypropyl cellulose and mixtures of the foregoing. Additional synthetic and/or semisynthetic polymers include, e.g., cellulose acetate phthalate (CAP), polyvinyl acetate phthalate (PVAP), hydroxypropyl methylcellulose phthalate, and/or acrylic polymers, such as methacrylic acid ester copolymers, zein, and the like. This list is not meant to be exclusive.

Preferably, the rate controlling material is prepared from one or more polysaccharide polymers capable of forming a release controlling matrix of polysaccharide polymers or gums. Preferred polysaccharide polymers include e.g., a heteropolysaccharide gum in combination with a polysaccharide capable of cross-linking with the heteropolysaccharide, such as, for example, a homopolysaccharide gum.

As reported previously in our U.S. Pat. Nos. 4,994,276, 5,128,143 and 5,135,757, the heterodisperse excipient comprising both hetero- and homopolysaccharide polymers or gums exhibit synergism, e.g., the combination of two or more polysaccharide gums produce a higher viscosity and faster hydration, when exposed to environmental fluids, than that which would be expected by either of the gums used alone and the resultant gel is faster forming and more rigid.

In general, the release controlling properties of a polysaccharide-based matrix of the present invention may be optimized when the ratio of a heteropolysaccharide gum to homopolysaccharide gum is from about 1:1 to about 1:10, although heteropolysaccharide gum in an amount ranging from about 8 to about 50 percent or more by weight, relative to the total weight of the polysaccharide blend may be employed. Preferably, a heteropolysaccharide gum in an amount ranging from about 8 to about 40 percent by weight of the homopolysaccharide gum, provides an acceptable slow release product. More preferably, the polysaccharide blend includes from about 8 to about 30 percent by weight of a heteropolysaccharide gum, and even more preferably, the polysaccharide blend includes about 12 percent by weight of a heteropolysaccharide gum.

One preferred heteropolysaccharide is xanthan gum and/or derivatives thereof. Xanthan gum is a high molecular weight (>$10^6$) heteropolysaccharide. Other preferred heteropolysaccharides that may be used according to the invention include derivatives of xanthan gum, such as deacylated xanthan gum, the carboxymethyl ether, and the polyethylene glycol ester of xanthan gum which may be readily substituted in whole or in part for a xanthan gum.

A preferred homopolysaccharide is a galactomannan, such as, for example, locust bean gum, a polysaccharide composed solely of mannose and galactose. The ordinary artisan will appreciate that other galactomannans may be readily employed in the preparation of the formulation according to the invention, although galactomannans which have higher proportions of unsubstituted mannose regions have been found to achieve more interaction with the xanthan gum. Thus, while other galactomannans such as guar and hydroxypropyl guar are suitable for use in the formulation according to the invention, locust bean gum, which has a higher ratio of mannose to galactose relative to guar and hydroxypropyl guar, is especially preferred.

Thus, in a most preferred embodiment the rate controlling material is a polysaccharide blend of a xanthan gum and a locust bean gum capable of cross-linking with the xanthan gum when the gums are exposed to an environmental fluid, thereby prolonging the release of the active agent component of the formulation.

In one preferred embodiment, the polysaccharide blend includes from about 10 to about 40 percent by weight of locust bean gum and more preferably, the polysaccharide blend includes about 18 percent by weight of locust bean gum.

The polysaccharide matrix also may include cationic cross-linking agents to provide additional stability and/or enhancement of the release controlling properties of the resulting matrix. The cationic cross-linking agent may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable cationic cross-linking agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride or mixtures thereof. Multivalent metal cations may also be utilized. However, the preferred cationic cross-linking agents are bivalent. Particularly preferred salts are calcium sulfate and sodium chloride.

The cationic cross-linking agents of the present invention are added in an amount effective to obtain a desirable increased gel strength due to linking with the homopolysaccharide. In one preferred embodiment, the cationic cross-linking agent comprises calcium sulfate, and is present in the sustained release excipient in an amount of about 10 percent, by weight of the excipient. The ratio of the homopolysaccharide to the cationic cross-linking agent is preferably from about 1.5:1 to about 3:1.

Optionally, the cationic cross-linking agent may also be an alkalizing agent according to the invention so that, e.g., the cationic cross-linking agent is, e.g., calcium hydroxide, serving as both a cross-linking agent and an alkalizing excipient.

In addition, any pharmaceutically acceptable inert diluent may be optionally blended with the polysaccharide gums. When an inert diluent is employed, it preferably comprises a pharmaceutically acceptable saccharide, including a monosaccharide, a disaccharide, a polyhydric alcohol, and/or mixtures of any of the foregoing.

Examples of suitable inert pharmaceutical diluents for use in the sustained release matrix preferably comprise a pharmaceutically acceptable saccharide, including a monosaccharide, a disaccharide or a polyhydric alcohol, a re-manufactured direct compression diluent and/or mixtures of any of the foregoing. Examples of suitable inert pharmaceutical diluents include sucrose, dextrose, lactose, microcrystalline cellulose, fructose, xylitol, sorbitol, starches, mixtures thereof and the like. However, it is preferred that a soluble pharmaceutical filler such as lactose, dextrose, sucrose, or mixtures thereof be used.

The inert diluent can be any pharmaceutically acceptable inert diluent, such as, a monosaccharide, a disaccharide, a polyhydric alcohol, and mixtures thereof. Water soluble diluents, such as sugars, are preferred. Water soluble diluents, e.g., sugars, include, for example, sucrose, dextrose, lactose, fructose, xylitol, sorbitol, and mixtures thereof, although microcrystalline cellulose and/or starch may be optionally employed with or without a water soluble diluent as previously described. Of the water soluble inert diluents, dextrose is generally preferred. The inert diluent is added to the formulation in amounts ranging from 5 to about 50 percent, by weight of the rate controlling polysaccharide mixture.

The inert diluent, as discussed above, is generally any pharmaceutically acceptable diluent, but is preferably a water soluble sugar, such as, for example, dextrose and/or combinations of any pharmaceutically acceptable inert diluent suitable for the purpose. The inert diluent is generally included in amounts ranging from 5 to about 50 percent, by weight of the total unit dosage form. Preferably, the inert diluent is present in amounts ranging from about 10 to about 30 percent, by weight, relative to the unit dosage form. In certain optional embodiments, the unit dosage form may be prepared with about 20% inert diluent If the mixture is to be manufactured without a wet granulation step, and the final mixture is to be tableted, it is preferred that all or part of the inert diluent comprise a pre-manufactured direct compression diluent. Such directed compression diluents are widely used in the pharmaceutical arts, and may be obtained from a variety of commercial sources. Examples of such premanufactured direct compression excipients include Emcocel® (microcrystalline cellulose, N.F.), Emdex® (dextrates, N.F.), and Tab-Fine® (a number of direct-compression sugars including sucrose, fructose and dextrose), all of which are commercial available from Edward Mendell Co., Inc., Patterson, N.Y.). Other direct compression diluents include anhydrous lactose (Lactose N.F., anhydrous direct tableting) from Sheffield Chemical, Union, N.J. 07083; Elcems® G-250 (Powdered cellulose, N.F.) from Degussa, D-600 Frankfurt (Main) Germany; Maltrin (Agglomerated maltodextrin) from Grain Processing, Muscatine, Iowa 52761; Neosorb 60® (Sorbitol, N.F., direct-compression) from Roquette Corp., 645 5th Ave., New York, N.Y. 10022; NuTab® (Compressible sugar, N.F.) from Ingredient Technology Inc., Pennsauken, N.J. 08110; Polytplasdone XL® (Crosspovidone, N.F., cross-linked polyvinylpyrrolidone) from GAF Corp., New York, N.Y. 10020; Primojel® (Sodium starch glycolate, N.F., carboxymethyl starch) from Generichem Corp., Little Falls, N.J. 07424; Solka Floc® (Cellulose floc) from Edward Mendell Co., Carmel, N.Y. 10512; Fast Flo Lactose (Lactose N.F., spray dried) from Foremost Whey Products, Baraboo, Wis. 53913 and DMV Corp., Vehgel, Holland; and Sta-Rx® 1500 (Starch 1500) (Pregelatinized starch, N.F., compressible) from Colorcon, Inc., West Point, Pa. 19486. However, it is preferred that a soluble pharmaceutical filler such as lactose, dextrose, sucrose, or mixtures thereof be used. In a preferred embodiment, the inert diluent is dextrose.

The tableting lubricant, e.g., Pruv® or other suitable lubricating substance, is generally included in amounts ranging from 1 to 3 percent by weight, or more, and is preferably included at about 1.5% by weight, relative to the weight of the unit dosage form.

Preferably, the controlled release matrix includes from about 30 to about 80 percent by weight of inert diluent and more preferably 65 percent by weight of inert diluent.

A controlled release formulation according to the invention may include an alkalizing agent or an acidifying agent, i.e., a pH modifying excipient, that is provided as part of the solid oral dosage form so that the incorporated active agent attains optimal dissolution and release from the matrix. This is accomplished, for example, by alkalizing the aqueous medium used to granulate the controlled release matrix when formulating an active agent that is characterized by solubility in an alkaline aqueous medium. Analogously, the aqueous medium used to granulate the controlled release matrix is acidified when formulating a sulfonylurea that is characterized by solubility in an acid aqueous medium. The sulfonylurea active agent can also be amphoteric, in which case the pH modifying excipient can be either acidic or basic.

Suitable basic excipients for rendering the aqueous medium at an alkaline pH, include a number of inorganic or organic bases which are pharmaceutically acceptable, in the dosage ranges used, including a monovalent metal alkali and/or a divalent metal alkali, such as, for example, sodium hydroxide solution, potassium hydroxide solution, calcium hydroxide, magnesium hydroxide, ammonia, tertiary sodium phosphate, diethanolamine, ethylenediamine, N-methylglucamine, or L-lysine and/or mixtures thereof. The molar ratio of active substance to basic excipient or mixtures of excipients is preferably from about 1:1.1 to 1:10, but a greater excess of base may also be advantageous in some cases. The alkalizing excipient includes, simply by way of example, sodium hydroxide, potassium hydroxide, calcium hydroxide, magnesium hydroxide, ammonia, tertiary sodium phosphate, diethanolamine, ethylenediamine, N-methylglucamine, 6 N-methyl-glucamine or L-lysine and/or mixtures thereof. The molar ratio of active substance to basic excipient or mixtures of excipients is preferably from about 1:1.1 to 1:10, but a greater excess of base may also be advantageous in some cases. The aqueous medium which is alkalized and granulated with the excipient according to the invention preferably has a pH ranging from about 7.0 to about 9.0 or more. The pH of the aqueous medium can also range from about pH 7.0 to about 8.0 or can be about pH 7.5. It is important that sufficient basic excipient is added to the formulation to ensure complete bioavailability in vivo.

In order to successfully provide a high level of bioavalability for glipizide that is orally administered in a release controlling matrix, glipizide is prepare in an alkalized dosage form. The alkalized dosage form may be prepared by any suitable art known method. In one example, an amount of a pharmaceutically acceptable alkalizing excipient is added to a pharmaceutically acceptable aqueous medium to raise the pH of that medium to 7.0 or greater. Preferably, the alkaline aqueous medium is least a pH of 7.5, to which is optionally added a surfactant and/or a polar solvent, e.g., polyalkylene glycol before incorporation into the polysaccharide matrix. In one embodiment, the polar solvent is preferably a polyethylene glycol or PEG. The glipizide is dissolved or dispersed in the alkalized aqueous medium. Optionally, glipizide is added to the alkalized medium before, together with, or after any optional surfactant, polar solvent and the like are dissolved or dispersed in the aqueous medium.

Suitable basic excipients include any inorganic or organic bases which are pharmaceutically acceptable, in the dosage ranges used, including a monovalent metal alkali and/or a divalent metal alkali, such as, for example, sodium hydroxide solution, potassium hydroxide solution, calcium hydroxide, magnesium hydroxide, ammonia, tertiary sodium phosphate, diethanolamine, ethylenediamine, N-methylglucamine, or L-lysine and/or mixtures thereof The molar ratio of active substance to basic excipient or mixtures of excipients is preferably from about 1:1.1 to 1:10, but a greater excess of base may also be advantageous in some cases.

In certain embodiments, the use of divalent metal hydroxide alkalizing agents such as calcium hydroxide may optionally be employed to optimize the degree of cross-linking in a polysaccharide based controlled release material to provide additional stability as required and to prolong the duration of release of the active agent therefrom.

In one preferred embodiment, the alkalizing excipient is mixed into the unit dosage formulation in an amount ranging from about 0.001 percent through about 10 percent by weight relative to the weight of the unit dosage form.

Preferably, the alkalizing excipient is added in an amount ranging from about 0.001 through about 1 percent by weight relative to the weight of the unit dosage form. In one preferred aspect, the alkalizing excipient is present at about 0.2 percent by weight, relative to the weight of the unit dosage form (e.g., tablet). Of course, the exact amount of alkalizing excipient to be employed will depend on the particular alkalizing agent and upon the buffering capacity of the aqueous medium and other components of the formulation employed. Thus, the artisan will appreciate that the optimum amount of alkalizing agent will be readily determined, for example, by a process of titration to the desired alkaline pH. In one embodiment, sodium hydroxide is preferably employed for this purpose.

The alkalizing agent or excipient can optionally be admixed with the polysaccharide rate controlling mixture and/or may be included in the mixture of the polysaccharide rate controlling mixture with the active agent. The alkalizing agent may be such a pH modifying excipient that is included in an amount ranging from about 0.001 percent through about 10 percent, by weight, or more, relative to the formulation. The pH modifying excipient can also be included in a range of from about 0.001 percent through about 1 percent, by weight, relative to the formulation. In another preferred embodiment, the alkalizing excipient is added in an amount of about 0.2 percent by weight, relative to the weight of the unit dosage form (e.g., tablet). Of course, the exact amount of alkalizing excipient to be employed will depend on the particular agent used. Thus, the artisan will appreciate that the optimum amount of alkalizing agent will be readily determined, for example, by a process of titration of the aqueous medium to the desired alkaline pH. In one embodiment, sodium hydroxide is preferably employed for this purpose.

An alkaline aqueous medium for use in formulating the matrix of the invention preferably has a pH ranging from about 7.0 to about 9.0, or more, so that the controlled release oral dosage form provides a fully bioavailable sustained release of sulfonylurea soluble in alkaline media for a period for about 24 hours or more. Analogously, an acidified aqueous solution for use in formulating the matrix of the invention preferably has a pH ranging from about pH 7.0 or less, e.g., from about pH 2 to about 6.9.

An acidifying agent for use in the present invention can be, for instance, sulfuric acid, phosphoric acid, hydrochloric acid and/or an organic acid such as citric, acetic or ascorbic acid or combinations or derivatives thereof. Suitable acidic agents or excipients are employed in a manner analogous to that described for alkalizing agents and include sulfuric and phosphoric acid as well as organic acids such as acetic acid, citric acid, ascorbic acid or any other acids or mixtures thereof that are pharmaceutically acceptable in the quantities employed. The acid excipient is preferably present in molar excess.

The formulation also includes a surfactant and/or a polar solvent, for example, polyalkylene glycols, including, e.g., polyethylene glycols or PEGs. The granulation is then mixed with a suitable tableting lubricant and the lubricated granulation is tableted or formed into any other suitable unit dosage form.

Advantageously, the solid controlled release oral dosage form is also prepared to include a surfactant or vehicle, including, e.g., a polar solubilizing agent, such as, polyalkylene glycols, e.g., the polyethylene glycols (PEGs) and/or polyvinylpyrrolidone, in an amount ranging from about 2% to about 40 percent, by weight of the formulation.

The polar solvent may be included in an amount effective to provide a final sustained release product having acceptable bioavailability. For example, in certain embodiments of the present invention, the polar solvent is included in an amount from about 2% to about 40% by weight of the final product. In another aspect, the polar solvent is included in an amount ranging from about 10% to about 30% of the final product, by weight. The artisan will appreciate that the polar solvent can be any pharmaceutically acceptable non-toxic agent suitable for the purpose. In a preferred embodiment, the polar solvent as described herein is preferably a polyalkylene glycol, including, e.g., polyethylene glycol (PEG). Such a PEG preferably has an average molecular weight ranging from about 1,000 to about 15,000, and more preferably from about 1,500 to about 12,000. In one preferred embodiment, the PEG is solid a room temperature, e.g., about 25 to 28 degrees C. A suitable PEG that is solid at room temperature is polyethylene glycol 3350. In an alternative embodiment a binding agent, such as polyvinylpyrrolidone ("PVP").

Optionally, the formulation according to the invention, prepared in unit dosage form, such as a tablet, is coated with an enteric and/or hydrophobic coating to provide increased sustained release of the active agent and/or to provide localized dissolution of the matrix in the intestinal tract instead of in the stomach.

For example, in certain embodiments of the invention, the tablet is coated with a sufficient amount of a hydrophobic polymer to render the formulation capable of providing a release of the medicament for up to 24 hours.

In other embodiments of the present invention, the tablet coating may comprise an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100-SSS.

In further embodiments, the dosage form may be coated with a hydrophilic coating in addition to or instead of the above-mentioned coatings. An example of a suitable material which may be used for such a hydrophilic coating is hydroxypropylmethyl-cellulose (e.g., Opadry®, commercially available from Colorcon, West Point, Pa.).

Cellulosic materials and polymers, including alkylcelluloses provide hydrophobic materials well suited for coating the solid oral dosage form according to the invention. Simply by way of example, one preferred alkylcellulosic polymer is ethylcellulose, although the artisan will appreciate that other cellulose and/or alkylcellulose polymers may be readily employed, singly or on any combination, as all or part of a hydrophobic coatings according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In other preferred embodiments of the present invention, the hydrophobic material comprising the controlled-release coating is a pharmaceutically acceptable acrylic polymer, including but not limited to acrylic acid and methacrylic acid copolymers, methyl methacrylate copolymers, ethoxyethyl methacrylates, cynao-ethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (methacrylic) esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from R öhm Tech, Inc. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit S does not swell at about pH<6.5 and is soluble at about pH>7. Eudragit RL and Eudragit RS are water swellable, and the amount of water absorbed by these polymers is pH-dependent, however, dosage forms coated with Eudragit RL and RS are pH-independent.

In one embodiment, ethyl cellulose or another suitable polymer as described hereinabove is employed as a coating material in an amount of from about 1% to about 30%, by weight of the total unit dosage form, may be so employed, and preferably in a weight ranging from about 3% to about 5%, by weight. In another embodiment, a pharmaceutically acceptable acrylic polymer suitable for the purpose in an amount ranging from about 1% to about 30% by weight of the total unit dosage form, and preferably in a weight ranging from about 3% to about 4%, by weight, of the total unit dosage form, may be so employed.

In certain preferred embodiments, the hydrophobic coating is ethylcellulose in an amount ranging from about 2% to about 10% of the weight of the coated unit dosage form. In a more preferred embodiment, the amount of the ethylcellulose coating ranges from about 3% to about 5% of the weight of the coated unit dosage form.

In other preferred embodiments, the hydrophobic coating is an acrylic polymer coating in an amount ranging from about 2% to about 10% of the weight of the coated unit dosage form. In a more preferred embodiment, the amount of the acrylic coating ranges from about 3% to about 4%, by weight, of the weight of the coated unit dosage form.

The coatings may be applied in any pharmaceutically acceptable manner known to those skilled in the art. In a preferred embodiment, the coating is applied via a fluidized bed or in a coating pan. The coated tablets may then be dried or cured, e.g., at about 60–70° C. for about 3–4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10 $\mu$ if applied via spray-coating or immersion-coating. Generally, in embodiments of the invention wherein a hydrophobic polymer or enteric coating is applied to the tablets, the tablets are coated to a weight gain from about 1 to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In another embodiment of the present invention, the tablet core includes an additional dose of the medicament included in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

Sustained release of the provided formulations is measured, e.g., in vitro in a dissolution medium have a non-neutral pH. For example, the in vitro dissolution profile of a sulfonylurea that is soluble in alkaline aqueous solution is measured 0.1N NaOH dissolution media by the Biodisc (USP Type III) method and a pH change design for the dissolution medium at 37° C. An analogous dissolution measurement is conducted for sulfonylureas soluble in acid aqueous media.

The solid controlled release oral dosage form according to the invention can be provided in any pharmaceutically acceptable unit dosage form, including tablets, caplets and beads and/or granules for administration, e.g., the later in a predetermined measured dosage form contained in gelatin capsules. Optionally, the unit dosage form according to the invention is coated with a sustained release hydrophobic coating composed of, for example, a pharmaceutically acceptable hydrophobic polymer. Any hydrophobic polymer suitable for the purpose may be employed to form all or part of such a coating. The sulfonylurea drug can be any antidiabetic sulfonylurea drug that benefits improvement in dissolution from an acid or basic pH-based formulation.

The invention also provides a method of treating diabetes, such as type II diabetes, by administering a solid controlled release oral dosage form prepared as described above to provide a sulfonylurea, e.g., glipizide, in a sustained release and bioavailable form, for a period of 12 hours or more, as measured, e.g., in vitro in 0.1N NaOH or 0.1N HCl dissolution media by the Biodisc (USP Type III) method and a pH change design for the dissolution medium at 37° C.

The controlled release oral dosage form of the present invention includes an active agent and a controlled release matrix and can be prepared by any art known method for effectively combining the required components.

The formulations according to the invention may be prepared by one or more of the following processes, although other, analogous methods may also be used.

The blend according to the invention may be produced by any suitable art known method for combining pharmaceutical excipients and active agents. The artisan will appreciate that the pH modifying agent, e.g., the alkalizing excipient or the acidifying excipient are added at any stage in the process where a sufficient aqueous environment is present in order to treat the sulfonylurea. In preferred embodiments, the rate controlling blend of polysaccharide gums is prepared by dry blending xanthan gum and locust bean gum together with an inert diluent, e.g., dextrose in a high speed mixer/granulator until the components are fully mixed. Agglomeration may be conducted by any art-known technique to yield an acceptable product.

In wet granulation techniques, the desired amounts of the polysaccharide, e.g., xanthan gum, locust bean gum and inert diluent are mixed together and thereafter a moistening agent such as pH modified aqueous solution (alkalized or acidified), optionally including polyethylene glycol, glycerol, alcohol or the like is added to prepare a moistened mass.

Preferably, the moistening agent is a desired amount of an aqueous dispersion of a hydrophobic polymer (e.g., Surelease®, an aqueous dispersion of ethylcellulose commercially available from Colorcon, Inc., West Point, Pa., USA) is added to the mixture by spraying while mixing, until the mixture is uniform. The resulting granulate is dried, e.g., in a fluid bed dryer to a low moisture content, e.g., less than 10 percent LOD. The dried granules are then milled through a fine mesh screen (e.g., from about 20 to about 30 mesh). In one preferred embodiment, the rate controlling matrix is prepared by blending polysaccharide gums capable of cross-linking each to the other, together with an inert diluent, a tableting lubricant and purified water. Alternatively, the powders can be premixed in dry form, and then the purified water is added.

The resulting granulate is then dried, e.g., in a fluidized bed drier to produce a rate controlling material. The rate controlling material is then blended with sulfonylurea that has been solubilized in a suitable pH modified aqueous medium including an optional polar solubilizing agent and optionally mixed with a tableting lubricant.

Of course, while the polysaccharide blend is conveniently pre-prepared, the artisan will appreciate that the entire formulation may be readily prepared in a single, batch or continuous process, without pre-preparing the polysaccharide blend.

The rate controlling polysaccharide mixture produced as described above is then dry blended, e.g., in a V-blender to achieve a uniform dry powder, during which time a solubilized composition including the active agent, e.g., the sulfonylurea, together with a suitable tableting lubricant, such as sodium stearyl fumarate (e.g., Pruv®) is added with further mixing to provide a uniform mixture for compression into unit dosage forms such as tablets, caplets or beads. In one embodiment, a polar solubilizer such as polyethylene glycol (PEG) is dissolved in an NaOH solution prior to the addition of the drug.

Dissolution rates of tablets prepared as described above are evaluated, for example, in vitro, in 0.1N NaOH in a U.S.P. type II dissolution apparatus at 50 RPM with 500 ml of dissolution media.

Further, the dissolution rate in vitro of the dosage form according to the invention was determined using the Biodisc (USP Type III) method and a pH change design for the dissolution medium at 37° C. gives a release of the drug of not more than 15% after 2 hours, between 20 and 60% after 8 hours and greater than 65% after 12 hours. Further still, the formulation according to the invention provides therapeutically effective blood levels of glipizide for a period of at least 24 hours in a patient.

Data presented in the Examples below also confirms that the advantageous dissolution profiles remain without significant change even after tablet storage times of up to 6 months, including storage at elevated temperature and relative humidity ("RH"), e.g., accelerated storage conditions of 40° C.–75% RH for 3 months or 25° C./60% RH for 6 months.

In order to exemplify the results achieved using the controlled release compositions of the present invention, the following examples are provided without any intent to limit the scope of the instant invention to the discussion therein. All parts and percentages are by weight unless otherwise indicated.

EXAMPLES 1–3

The data presented by the Examples, hereinbelow, compares the dissolution properties for glipizide tablets prepared with various drug:gum ratios and with varying amounts of an alkalizing excipient and/or polar solvent. Generally, the higher the drug to gum ratio, the slower the release rate during a period of from 1–12 hours. Thus, a drug to gum ratio of 1:15 provided the most prolonged duration of glipizide release in the absence of a polar solvent such as a solid PEG.

A rate controlling matrix material is prepared by dry blending 12% w/w xanthan gum, 13% w/w locust bean gum and 65% w/w dextrose in a high speed mixer/granulator for 3 minutes with the chopper on. Surelease® is then sprayed into the other ingredients with chopper on fast speed for 2–5 minutes. Granulation is continued for an additional 5 minutes. The granules are then dried in a fluid bed dryer to a moisture content of less than 10% (e.g. 4–7% LOD). The dried granules are milled using a 20 mesh screen to product a rate controlling matrix material for use in Examples 1 through 9.

TABLE I

Rate Controlling Polysaccharide Mixture Composition

| Compound | % w/w |
|---|---|
| 1. Xanthan Gum | 12 |
| 2. Locust Bean Gum | 18 |
| 3. Dextrose | 65 |
| 4. Surelease ® | 5 |
| 5. Purified Water* | |

*Removed during processing

In Examples 1, 2 and 3, varying amounts of controlled release matrix blend is dry blended in a V blender with active agent for 10 minutes. A suitable tableting lubricant (e.g. Pruv®, sodium stearyl fumarate) is added and the resulting mixture is blended for another 5 minutes. This final mixture is compressed into tablets. The % composition of this formulation is presented in Table II for Examples 1,2 and 3 where the effect of drug:gum ratio on the release rate is provided.

TABLE II

Tablet Formulation - Example 1, 2, 3

| | Example No. | | |
|---|---|---|---|
| Component | 1 mg/Tab | 2 mg/Tab | 3 mg/Tab |
| 1. Matrix Material (Table I) | 83.3 | 166.7 | 250.0 |
| 2. Glipizide | 5.0 | 5.0 | 5.0 |
| 3. Pruv ® | 1.4 | 3.3 | 3.9 |
| 4. Dextrose | — | 43.7 | — |
| Total Tablet Wt.(mg) | 89.7 | 218.7 | 258.9 |
| Drug:Gum | 1:5 | 1:10 | 1:15 |
| Hardness (kp) | 3.3 | 5.32 | 7.0 |

Each of the formulations of Examples 1, 2 and 3 is evaluated for in vitro release in 500 mLs of 0.1 N NaOH solution as dissolution media in a USP Type II dissolution apparatus at 50 rpm. The dissolution data is presented in Table III, below.

TABLE III

Apparatus: USP Type II; Media = 0.1 N NaOH; Agitation: 50 rpm

| | Example # (% dissolved) | | |
|---|---|---|---|
| Time (Hrs) | #1 | #2 | #3 |
| | 0 | 0 | 0 |
| 1 | 26.9 | 20.8 | 18.9 |
| 2 | 44.1 | 33.5 | 30.0 |
| 4 | 67.0 | 50.8 | 47.2 |
| 8 | 88.0 | 73.9 | 71.9 |
| 10 | 93.4 | 82.3 | 78.4 |
| 12 | 99.3 | 85.9 | 84.8 |

The drug to matrix ratio in Examples 1, 2 and 3 was varied from 1:5 through 1:15. From the data it appears that as the amount of gum in the formulation was increased, a decrease in % drug dissolution resulted. However, no significant difference was seen for the 1:10 and 1:15 drug to gum ratio formulations (Examples 2 and 3).

EXAMPLES 4 AND 5

Controlled release matrix material produced in accordance with the procedure for examples 1–3 is mixed with prescreened drug and passed through a 30 mesh screen and blended for 5 minutes. 43.7 mg of Polyethylene Glycol 3350 (example 4) or 43.7 g of PVP (example 5) is added and the mixture is blended for 2 minutes. Pruv® is then added and blended for 2 minutes (optionally, the lubricant and PEG can be mixed prior to spraying the blend). The resulting mixture is compressed into tablets for use in examples 4 and 5.

TABLE IV

Tablet Formulation

| | Example Nos. | |
|---|---|---|
| Component | 4 mg/Tab | 5 mg/Tab |
| Matrix material (Table I) | 166.7 | 166.7 |
| Glipizide | 5 | 5 |
| Pruv ® | 3.3 | 3.3 |
| Polyethylene glycol 3350 | 43.7 | — |
| PVP | — | 43.7 |
| Purified water* | | |
| Tablet Weight (mg) | 218.7 | 218.7 |

*Removed during processing

The tablets so produced for examples 4 and 5 are evaluated for in vitro release/dissolution in the following dissolution media: (a) DI water at pH 9.00 (b) DI water (c) DI water to which NaOH was added at the end of testing period. The dissolution conditions were:

| Apparatus: | USP Type III |
|---|---|
| Volume of Dissolution Medium: | 250 ml |
| Agitation: | 15 cpm |

The dissolution data is presented in Table V.

TABLE V

| Dissolution Media Time | #4 % Dissolved | | | #5 % Dissolved | | |
|---|---|---|---|---|---|---|
| (Hrs) | A | B | C | A | B | C |
| 0 | 0 | 0 | 0 | 0 | 0 | 0 |
| 2 | 25.7 | 48.1 | 69.9 | 28.1 | 77 | 86 |
| 4 | 52.2 | 83.5 | 93.8 | 57.6 | 83 | 94 |
| 6 | 80.4 | 84.8 | 95.7 | 99.2 | 83 | 94 |

Dissolution Media:
A = Deionized ("DI") water at pH 9.0
B = DI water
C = DI water with addition of NaOH before analysis.

The data confirms that both formulations (with the two different water-soluble carriers) have comparable dissolution profiles. However, the percentage in deionized water alone did not allow all of the drug to be released from the matrix.

EXAMPLE 6

0.5 mg NaOH is dissolved in water and heated to 55° C. 50 mg PEG is dissolved in the resulting NaOH solution and 5 mg glipizide is then also dissolved in the solution. 166.7 mg of matrix is then granulated in a high shear mixer with the drug/NaOH/PEG solution. The granules are dried and mixed, then blended with 3.4 mg of Pruv® and compressed into a tablet.

TABLE VI (Example 6)

| Component | Example 6 mg/tablet |
|---|---|
| Matrix material/Tablet | 166.7 |
| Glipizide | 5 |
| PEG 3350 | 50 |
| NaOH | 0.5 |
| Pruv ® | 3.4 |
| Water* | |
| Tablet Weight (mg) | 225.6 |

*Removed during processing

When the dissolution tests of tablets so made are conducted in deionized ("DI") water, it is surprisingly found that all the drug was being released from the matrixed tablet as presented in Table VII below. Both Type II USP apparatus and the biodisc (Type III) dissolution apparatus were employed using DI water alone, DI water adjusted to pH 7.5, and DI water adjusted to pH 9.00.

TABLE VII

| | Dissolution Apparatus | | | | | |
|---|---|---|---|---|---|---|
| | USP Type II | | | USP Type III | | |
| Dissolution Media | A | B | C | A | B | C |
| | Glipizide | | | Glipizide | | |
| Time (hrs) | % Dissolved | | | % Dissolved | | |
| 0 | 0 | 0 | 0 | 0 | 0 | 0 |
| 1 | 18.2 | 16.6 | | 33.3 | 38.4 | 11.5 |
| 2 | 30.0 | 30.8 | | 56.5 | 82.9 | 39.1 |
| 4 | 59.1 | 61.3 | | 62.3 | 100.1 | 72.1 |
| 6 | 87.1 | — | | 75.1 | 100.6 | 93.1 |
| 8 | 101.8 | 103.8 | | 96.7 | 101.2 | 105.4 |
| 12 | 102.0 | 103.9 | | 96.8 | 101.8 | 101.1 |

A = DI water at pH 7.5
B = DI water
C = D1 water at pH 9.00

The data confirms that this formulation released essentially all the drug over a 12 hour period even in a purified ("P") water dissolution media. This was a surprising finding which was further studied below.

EXAMPLE 7

The formula for tablets used in Example 7 is presented in Table VIII. Such tablets are made according to the process set out in examples 1–3. Note that in this case no water soluble carrier is present in the formulation.

0.5 mg NaOH is dissolved in water and heated to 55° C. 5.0 mg of Glipizide is added to the solution. 133.3 mg of matrix material and 25.0 mg of dextrose is added to the solution and then granulated in a high shear mixer. The granules are dried and mixed, then blended with Pruv® and compressed into a core tablet.

TABLE VIII (Example 7 Formula)

| Component | mg/Tablet |
|---|---|
| Matrix material | 133.3 |
| Glipizide | 5.0 |
| Dextrose | 25.0 |
| Sodium Hydroxide | 0.5 |
| Pruv ® | 2.5 |
| Water* | |
| Tablet Wt | 166.3 |

*Removed during processing

Dissolutions tests on tablets so produced were carried out in a biodisc apparatus (USP Type III) and the pH of the dissolution medium was raised from 1.5 to 7.5 with time in order to better simulate the GI tract as follows in Table X.

Core tablets are coated with either Ethylcellulose (3,4, 5%) or with an enteric acrylic polymer (3–4%). The dissolution data for these coated tablets is presented below in Table X.

TABLE X

Dissolution Data for Example 7

| Time (hours) | Core Tablets % Glipizide Dissolution | Ethylcellulose Coating Coating Level | | | Enteric Acrylic Polymer Coating Coating Level | |
|---|---|---|---|---|---|---|
| | | 3%* | 4%* | 5%* | 3%* | 4%* |
| 0 | 0 | 0 | 0 | 0 | 0 | 0 |
| 1 | 6.0 | 0 | 0 | 0 | 0 | 0 |
| 2 | 11.4 | 0 | 0 | 0 | 0 | 0 |
| 4 | 34.2 | 2.6 | 1.0 | 0.0 | 11.1 | 8.8 |
| 6 | 59.5 | 11.5 | 9.5 | 3.4 | 36.2 | 32.0 |
| 8 | 77.4 | 20.7 | 17.5 | 10.8 | 60.6 | 57.4 |
| 12 | 107.4 | 38.0 | 35.4 | 24.1 | 85.2 | 89.4 |

*% Glipizide dissolved.

The tablets coated with Ethyl cellulose gave a relatively slow release profile. The enteric coated tablets provide an initial lag before releasing the drug.

EXAMPLE 8

0.5 mg sodium hydroxide is dissolved in purified water to which is added the glipizide. The solution is mixed until all solids are dissolved. 5 mg of PEG 3350 is added to this solution and dissolved. The matrix material and Dextrose are blended in a high shear mixer and the active agent is added to the high shear mixer and granulated. The granulation is dried to an LOD of about 5% and the granules are milled using a Fitz mill. 2.6 mg of sodium stearyl fumarate is added and the resulting mixture is blended in a P-K Blender.

The mixture is compressed to form a tablet of the desired weight. The core tablets can be optionally coated, as desired, in a suitable coating pan (e.g. Vector LDCS coating unit). The instant tablets are prepared with a 7% w/w enteric coating.

TABLE XI

Example 8. Formula

| Component | mg/Tablet |
|---|---|
| Matrix material (Tablet 1) | 133.3 |
| Glipizide | 5 |
| Dextrose | 25 |
| PEG 3350 | 5 |
| Sodium Hydroxide | 0.5 |
| Sodium Stearyl Fumarate | 2.6 |
| Tablet Wt (mg) | 171.4 |

The core tablets are film coated with an enteric acrylic polymer at 7% w/w.

The dissolution of these tablets having a 7% w/w enteric coat in USP Type III and the USP Type II apparatus is presented in Table XII.

TABLE XII

Dissolution Data For Example 8 Type Ii And Type III, pH Change Method

| | % Glipizide Dissolved | |
|---|---|---|
| Time Hrs. | Type 11* 150 rpm | Type III** 15 cpm |
| 0 | 0 | 0 |
| 1 | 1.8 | 0 |
| 2 | 9.9 | 0 |
| 3 | 16.9 | — |
| 4 | 29.9 | 0.9 |
| 6 | 69 | 21.2 |
| 8 | 91.1 | 43.2 |
| 10 | 101.1 | — |
| 12 | — | 77 |

*pH change, 1st hr. pH 1.5; 2nd to 24 hrs. pH 7.5
**pH change, 0–1 hr. pH 1.5; 1–2 hrs. pH 3.5, 3–6 hrs. pH 5.5, 5–12 hrs. pH 7.5

Tablets so manufactured are packaged in high density polyethylene (HDPE) bottles with caps and subjected to accelerated storage conditions of 40° C.–75% relative humidity ("RH") for 3 months. Samples are analyzed at 1, 2, and 3 months. Samples are also stored at 25° C./60% RH for 6 months. Data regarding dissolution rates for these and tablet samples stored at ambient room temperature as bulk tablets are analyzed and stability data is presented in Table XIII below.

TABLE XIII

Accelerated and RT Stability Data (Example 8) Glipizide Coated Tablets

| | Assay for | % Glipizide Dissolved Type III, Dissolution, pH Change Method | | |
|---|---|---|---|---|
| Time | Glipizide (% Label) | 2 hrs. | 8 hrs. | 12 hrs. |
| Initial | 97.0 | 0.0 | 43.2 | 77 |
| 40° C.-75% R H 1 Mo. | 98.9 | 3.5 | 38.9 | 76.8 |
| 2 Mo. | 97.6 | 0.0 | 39.3 | 78.4 |
| 3 Mo. | 99.4 | 0.0 | 37.3 | 76.5 |
| 25° C.-60% RH 6 Mo. Ambient | 96.5 | 0.0 | 44.8 | 79.9 |
| Room Temp. 3 Mo. | | | | |

As will be appreciated from the data of Table XIII, dissolution profiles exhibit no significant changes after storage for 1, 2, 3 and 6 months. This data demonstrates that the formulations according to the present invention have the stability profile required for pharmaceutical products.

EXAMPLE 9

The formula for a 10 mg glipizide dosage tablet is presented in Table XIV, below.

The procedure for the preparation of tablets made according to the formula of Table XIV is the same as employed in Example 6. The core tablets are coated with an acrylic enteric coating to a 4% weight gain.

TABLE XIV

Example 9, Formula

| Compound | mg/tablet |
|---|---|
| Polysaccharide Blend (Tablet 1) | 250.0 |
| Glipizide | 10.0 |
| PEG 3350 | 10.0 |
| Dextrose | 70.0 |
| Sodium Hydroxide (in Core) | 1.0 |
| Pruv ® (Sodium Stearyl Fumarate) | 5.0 |
| Water | |
| Core Tablet Wt. | 346.0 |

Dissolution test is shown in Table XVI and is carried out using a biodisc apparatus (USA Type III) with the pH of the dissolution medium being raised from 1.5 to 7.5 at time intervals according to Table XV.

TABLE XV

| Time (Hrs.) | pH |
|---|---|
| 0–1 | 1.5 |
| 1–3 | 3–5 |
| 2–4 | 5.5 |
| 4–20 | 7.5 |

TABLE XVI

DISSOLUTION DATA FOR EXAMPLE 9

| Time Hrs. | % Glipizide Dissolved Type III, 15 cpm |
|---|---|
| 0 | 0 |
| 2 | 0 |
| 4 | 1.8 |
| 8 | 31.1 |

TABLE XVI-continued

DISSOLUTION DATA FOR EXAMPLE 9

| Time Hrs. | % Glipizide Dissolved Type III, 15 cpm |
| --- | --- |
| 12 | 68.6 |
| 20 | 92.1 |

EXAMPLES 10–11

In Example 10 a single dose randomized crossover biostudy is conducted in the fasted condition to compare the bioavailability of tablets of Example 8 to a commercially available product with the same dosage strength but a different release mechanism generally prescribed as a once-a-day adjunct to a controlled diet for the control of hyperglycemia and associated symptomatology in patients with non-insulin-dependant diabetes mellitus. This study is conducted in 12 normal, healthy male volunteers.

In Example 11, a single dose randomized crossover biostudy is conducted in the fed condition to compare the bioavailability of tablets of Example 8 of the present invention to the same commercially available product as in Example 10. This study is also conducted in 12 normal healthy male volunteers. The biostudy results from examples 10 and 11 are presented in Table XV, below.

TABLE XVII

BIOSTUDY RESULTS FOR EXAMPLES 10–11

| Example No. | | Tmax(Hr) | AUC (nghv/ml) | Cmax (mg/mL) |
| --- | --- | --- | --- | --- |
| 10 | Test Fasted | 8 hrs. | 4716 | 268 |
|    | Ref. Fasted | 6 hrs. | 5107 | 284 |
| 11 | Test Fed | 12 hrs. | 4263 | 227 |
|    | Ref Fed | 8 hrs. | 4773 | 277 |
| 10 | Test Fasted: Ref Fasted | 1.25 | 0.90 | 0.94 |
| 11 | Test Fed: Ref Fed | 1.83 | 0.80 | 0.82 |

All patents, patent applications and other aforementioned references are herein incorporated by reference in their entirety.

The scope of the following claims is intended to encompass all obvious changes in the details, materials and arrangement of parts that will occur to one of ordinary skill in the art.

What is claimed is:

1. A method of treating diabetes comprising administering a sustained release dosage form for oral administration comprising:
   a) a therapeutically effective amount of sulfonylurea suspended or dissolved in an alkaline aqueous medium; and,
   b) a controlled release matrix comprising a gelling agent, and an inert diluent; wherein: the ratio of gelling agent to inert diluent is from about 1:8 to about 8:1; and the gelling agent comprises a heteropolysaccharide and a homopolysaccharide in a ratio of from about 3:1 to about 1:3.

2. The method of claim 1, wherein said dosage form is effective for once a day oral administration.

3. The method of claim 1, wherein the controlled release matrix comprises: xanthan gum; locust bean gum; and dextrose.

4. The method of claim 1, wherein the controlled release matrix comprises: 12.0% w/w xanthan gum; 18% w/w locust bean gum; and, 65% w/w/dextrose.

5. The method of claim 4, wherein the controlled release matrix additionally comprises ethylcellulose.

6. The method of claim 5, wherein the ethylcellulose is present in the amount of 5% w/w.

7. The method of claim 1, wherein the inert diluent is selected from the group consisting of a monosaccharide, a disaccharide, a polyhydric alcohol, microcrystalline cellulose, starch and mixtures thereof.

8. The method of claim 7, wherein the inert diluent is selected from the group consisting of sucrose, dextrose, lactose, fructose, xylitol, sorbitol and mixtures thereof.

9. The method of claim 8, wherein the inert diluent is dextrose.

10. The method of claim 1, wherein the controlled release matrix is wet granulated with an aqueous solution comprising an alkalizing excipient present in an amount effective to provide a pH ranging from about 7.0 to about 9.0 prior to incorporation with said suspension or solution of sulfonylurea.

11. The method of claim 1, wherein said alkaline aqueous medium is an aqueous solution comprising an alkalizing excipient present in an amount effective to provide a pH ranging from about 7.0 to about 9.0.

12. The method of claim 11, wherein the alkalizing excipient is selected from the group consisting of a monovalent metal alkali and a divalent metal alkali.

13. The method of claim 12, wherein the alkalizing excipient is selected from the group consisting of sodium hydroxide, potassium hydroxide, calcium hydroxide, magnesium hydroxide, ammonia, tertiary sodium phosphate, diethanolamine, ethylenediamine, N-methylglucamine, L-lysine and mixtures thereof.

14. The method of claim 12, wherein the alkalizing excipient is present in an amount ranging from about 0.001 percent through about 10 percent by weight of the formulation.

15. The method of claim 1, wherein the oral dosage form is selected from the group consisting of a tablet, a caplet and a capsule.

16. The method of claim 15 wherein the capsule contains a plurality of beads or particles.

17. The method of claim 1, wherein the oral dosage form is further coated with a sustained release hydrophobic coating comprising a pharmaceutically acceptable hydrophobic polymer.

18. The method of claim 17, wherein the hydrophobic coating is selected from the group consisting of ethyl cellulose, acrylic polymers, and methacrylic polymers in an amount of from about 1 to about 30 percent, by weight of the total oral dosage form.

19. The method of claim 1, wherein said sulfonylurea is glipizide or a pharmaceutically acceptable salt thereof.

20. The method of claim 1, wherein said heteropolysaccharide is xanthan gum.

21. The method of claim 1, wherein said homopolysaccharide is locust bean gum.

22. The method of claim 1, wherein said heteropolysaccharide is xanthan gum and said homopolysaccharide is locust bean gum.

23. A method of treating diabetes comprising administering a controlled release oral dosage form for once a day administration of a sulfonylurea manufactured by the steps comprising:
   a) suspending or dissolving a therapeutically effective amount of a sulfonylurea in an alkaline aqueous medium, wherein said sulfonylurea is selected from the group consisting of tolbutamide, chiorpropamide, tolazamide, aetohexamide, glyburide, glibomuride, glisoxepide, glipizide and gliclazide;
b) granulating a controlled release matrix with the suspension or solution of step a);
c) tableting the granulation.

24. The method of claim 23, wherein a tableting agent is added to the granulation prior to tableting.

25. The method of claim 23, wherein said sulfonylurea is glipizide or a pharmaceutically acceptable salt thereof.

26. The method of claim 23, wherein said controlled release matrix is comprised of xanthan gum, locust bean gum and dextrose.

27. The method of claim 26, wherein the controlled release matrix comprises about 12% w/w xanthan gum, about 18% w/w locust bean gum and about 65% w/w dextrose.

28. The method of claim 23, wherein said matrix comprises a heteropolysacharide, a homopolysacharide and in inert diluent.

29. The method of claim 26, wherein said heteropolysaccharide is xanthan gum.

30. The method of claim 26, wherein said bomopolysaccharide is locust bean gum.

31. The method of claim 26, wherein said heteropolysaccharide is xanthan gum and said homopolysaccharide is locust bean gum.

32. The method of claim 23 wherein the matrix is first granulated with an aqueous medium made alkaline by a pharmaceutically acceptable alkalizing excipient present in an amount effective to provide a pH ranging from at least 7.0 to about 9.0.

33. The method of claim 1, wherein a polyalkylene glycol is added to the alkaline aqueous medium of step a.

34. The method of claim 33, wherein the polyalkylene glycol is polyethylene glycol.

35. The method of claim 23, wherein a polyalkylene glycol is added to the alkaline aqueous medium of step a.

36. The method of claim 35, wherein the polyalkylene glycol is polyethylene glycol.

37. The method of claim 1, wherein a binding agent is added to the alkaline aqueous medium of step a.

38. The method of claim 37, wherein the binding agent is polyvinylpyrrolidone.

39. The method of claim 23, wherein a binding agent is added to the alkaline aqueous medium of step a.

40. The method of claim 39, wherein the binding agent is polyvinylpyrrolidone.

41. A method of treating type II diabetes comprising administering an at least once a day solid controlled release oral dosage form comprising:
a) an effective amount of glipizide in an alkaline aqueous medium or a salt thereof,
b) a granulation comprising a controlled release matrix and an aqueous medium made alkaline by addition of a pharmaceutically acceptable alkalizing excipient present in an amount effective to provide a pH ranging from at least 7.0 to about 9.0, said matrix comprising xanthan gum, locust bean gum and an inert diluent.

* * * * *